(12) United States Patent
Kim et al.

(10) Patent No.: US 11,564,796 B2
(45) Date of Patent: *Jan. 31, 2023

(54) ASSEMBLY-TYPE DEVICE FOR TREATMENT OF TRICUSPID REGURGITATION

(71) Applicant: TAU PNU MEDICAL CO., LTD., Busan (KR)

(72) Inventors: June Hong Kim, Busan (KR); Min Ku Chon, Yangsan-si (KR)

(73) Assignee: TAU-PNU MEDICAL., LTD., Busan (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/747,431

(22) Filed: Jan. 20, 2020

(65) Prior Publication Data

US 2020/0229916 A1 Jul. 23, 2020

(30) Foreign Application Priority Data

Jan. 21, 2019 (KR) ........................ 10-2019-0007774

(51) Int. Cl.
*A61F 2/24* (2006.01)

(52) U.S. Cl.
CPC ...... *A61F 2/246* (2013.01); *A61F 2210/0014* (2013.01); *A61F 2220/0008* (2013.01); *A61F 2250/0003* (2013.01)

(58) Field of Classification Search
CPC .................... A61F 2/246; A61F 2/2466; A61F 2220/0008; A61F 2250/0003; A61F 2220/0016
See application file for complete search history.

(56) References Cited

U.S. PATENT DOCUMENTS 7,854,762 B2 12/2010 Speziali et al.
8,486,136 B2 7/2013 Maurer et al.
(Continued)

FOREIGN PATENT DOCUMENTS

CN 102869318 A 1/2013
EP 3662866 A4 5/2021
(Continued)

OTHER PUBLICATIONS

International Preliminary Report on Patentability dated Feb. 4, 2020 of PCT/KR2018/008525.
(Continued)

*Primary Examiner* — Jennifer Dieterle
*Assistant Examiner* — Rebecca Lynee Zimmerman
(74) *Attorney, Agent, or Firm* — Justin Kim

(57) ABSTRACT

An assembly-type device for the treatment of tricuspid regurgitation is proposed. The assembly-type device includes: a fixing member for the pulmonary artery, the fixing member installed in the pulmonary artery; a connecting tube provided with a connecting tube lumen formed therein to be movable along a connecting wire; an assembly part provided with a first assembly coupled to a lower end of the fixing member for the pulmonary artery and a second assembly coupled to an upper end of the connecting tube, wherein the fixing member for the pulmonary artery and the connecting tube are assembled together; a fixing member for inferior vena cava, the fixing member coupled to a lower end of the connecting tube and installed in the inferior vena cava; and a blocking part coupled to one side of the connecting tube and obliquely passing through a tricuspid valve to block an orifice of the tricuspid valve.

15 Claims, 12 Drawing Sheets

(56) References Cited

U.S. PATENT DOCUMENTS

| | | |
|---|---|---|
| 9,474,605 B2 | 10/2016 | Rowe et al. |
| 11,357,485 B2 | 6/2022 | Kim |
| 2005/0027351 A1 | 2/2005 | Reuter et al. |
| 2006/0064059 A1 | 3/2006 | Gelfand et al. |
| 2007/0198082 A1 | 8/2007 | Kapadia et al. |
| 2007/0239270 A1 | 10/2007 | Mathis et al. |
| 2009/0240326 A1 | 9/2009 | Wilson et al. |
| 2011/0077733 A1 | 3/2011 | Solem |
| 2011/0112632 A1 | 5/2011 | Chau et al. |
| 2011/0257677 A1 | 10/2011 | Carr, Jr. et al. |
| 2012/0172844 A1 | 7/2012 | Mullen |
| 2013/0274645 A1 | 10/2013 | Ferrari |
| 2013/0325110 A1 | 12/2013 | Khalil et al. |
| 2013/0338763 A1* | 12/2013 | Rowe ............ A61F 2/2427 623/2.11 |
| 2015/0366556 A1* | 12/2015 | Khairkhahan ..... A61B 17/0487 606/232 |
| 2016/0213472 A1 | 7/2016 | Kim |
| 2016/0228246 A1 | 8/2016 | Zimmerman |
| 2017/0119489 A1 | 5/2017 | Kim |
| 2021/0085451 A1 | 3/2021 | Kim |

FOREIGN PATENT DOCUMENTS

| | | |
|---|---|---|
| EP | 3662867 A4 | 5/2021 |
| JP | 1992507208 | 12/1992 |
| JP | H11509450 A | 8/1999 |
| JP | 2008536592 A | 9/2008 |
| KR | 20120051936 A | 5/2012 |
| KR | 1020120051936 A | 5/2012 |
| KR | 20130074823 A | 7/2013 |
| KR | 1020130074823 A | 7/2013 |
| KR | 101563172 B1 | 10/2015 |
| KR | 20150144568 A | 12/2015 |
| KR | 1020150144568 A | 12/2015 |
| KR | 20170034088 A | 3/2017 |
| KR | 101730387 B1 | 4/2017 |
| KR | 20170044065 A | 4/2017 |
| KR | 1020170044065 A | 4/2017 |
| KR | 101805679 B1 | 12/2017 |
| WO | 2019027175 A1 | 2/2019 |
| WO | 2019027183 A3 | 3/2019 |

OTHER PUBLICATIONS

International Preliminary Report on Patentability of corresponding international application No. PCT/KR2018/008409 dated Feb. 4, 2020.

International search report (ISR) and written opinion of corresponding international application No. PCT/KR2018/008409 dated Oct. 15, 2018 and Oct. 16, 2018, respectively.

International search report (ISR) of PCT/KR2018/008525 dated Mar. 1, 2019.

* cited by examiner

ASSEMBLY-TYPE DEVICE FOR TREATMENT OF TRICUSPID REGURGITATION

CROSS REFERENCE TO RELATED APPLICATION

The present application claims priority to Korean Patent Application No. 10-2019-0007774, filed Jan. 21, 2019, the entire contents of which is incorporated herein for all purposes by this reference.

BACKGROUND OF THE INVENTION

Field of the Invention

The present invention relates to an assembly-type device for a treatment of tricuspid regurgitation. More particularly, the present invention relates to an assembly-type device for a treatment of tricuspid regurgitation, wherein the device is provided for treating tricuspid regurgitation (TR), which is a disease where blood from the right ventricle flows back into the right atrium through an empty space (i.e., orifice) formed by incomplete closing of a tricuspid valve (TV), and wherein the device is easily assembled in a patient's body and the position of a blocking part is easily adjusted.

Description of the Related Art

The heart is composed of four hollow chambers: the left atrium, the left ventricle, the right atrium, and the right ventricle, and are connected to the aorta, the vena cava, the pulmonary artery, and the pulmonary vein. There are valves between the ventricles and the atria. The valve between the left atrium and the left ventricle is called the mitral valve, and the valve between the right atrium and the right ventricle is called the tricuspid valve.

The heart repeats contraction and relaxation to enable blood to circulate. In the systolic phase of the heart, the blood in the heart moves to blood vessels, wherein the blood in the right ventricle flows to the pulmonary artery and the blood in the left ventricle flows to the aorta.

However, when a valve is not working properly, blood backflow occurs, thereby causing the blood that must flow into the blood vessels to flow back to the atrium during the cardiac contraction.

Tricuspid regurgitation (TR) refers to a symptom of blood backflow from the right ventricle to the right atrium during cardiac contraction through an orifice, wherein, since the tricuspid valve (TV) between the right atrium and the right ventricle is stretched or torn, or since the chordae tendineas holding the tricuspid valve is broken, the tricuspid valve closes incompletely when the tricuspid valve needs to be closed, resulting in the orifice. This is also called tricuspid valve insufficiency.

U.S. Pat. Nos. 8,486,136 B2, 7,854,762 B2, and 9,474,605 B2 disclose devices for treating tricuspid regurgitation, and the devices for treating tricuspid regurgitation are inserted into the superior vein cava, the tricuspid valve, and the right ventricle in sequence, and block the orifice of the tricuspid valve, thereby treating the tricuspid regurgitation. In the devices for the treatment of tricuspid regurgitation, an anchor installed at one end of each device is fixed to the ventricle, and the other end thereof is fixed to the outside of the heart by passing through the superior vein cava. Accordingly, the blocking part of the related patents is placed in an unstable state of passing through the centerline of the orifice of the tricuspid valve with a longitudinal orientation and floating within the heart.

The fixing device of the conventional devices for treatment of tricuspid regurgitation is fixed to the ventricle and a position outside the heart. Since the heart is positioned above the diaphragm and the heart moves up and down according to the vertical movement of the diaphragm during breathing, the conventional devices for the treatment of tricuspid regurgitation move up and down according to the movement of the diaphragm during the breathing. When this movement is repeated, there occurs a problem in that the blocking part is positioned off the centerline of the orifice of the tricuspid valve. When the blocking part deviates from the centerline of the orifice of the tricuspid valve, the function of the tricuspid valve is adversely affected.

Moreover, in Korean Patent No. 10-1805679 invented by the present inventor, a device for the treatment of the tricuspid regurgitation, the device having a blocking part which is obliquely passed through the tricuspid valve by connecting the coronary sinus and the ventricular septum, is filed and is registered. The blocking part is stably positioned inside the heart, but requires a relatively difficult treatment with passing through the ventricular septum.

DOCUMENTS OF RELATED ART (Patent Document 1) U.S. Pat. No. 8,486,136 B2 (Jul. 16, 2013)
(Patent Document 2) U.S. Pat. No. 7,854,762 B2 (Dec. 21, 2010)
(Patent Document 3) U.S. Pat. No. 9,474,605 B2 (Oct. 25, 2016)
(Patent Document 4) KR 101805679 (Nov. 30, 2017)

SUMMARY OF THE INVENTION

The present invention is to provide an assembly-type device for a treatment of tricuspid regurgitation that may simply treat tricuspid regurgitation by passing through the inferior vena cava, the tricuspid valve, and the pulmonary artery in sequence in order to solve the problem of the related art.

In addition, the present invention is to provide an assembly-type device for a treatment of tricuspid regurgitation that may be obliquely passed through the orifice of the tricuspid valve to stably block the orifice of the tricuspid valve.

In addition, the present invention is to provide an assembly-type device for a treatment of tricuspid regurgitation that is configured to easily maintain the centerline orientation of the orifice of the tricuspid valve without being affected by the movement of the diaphragm during breathing.

In addition, the present invention is to provide an assembly-type device for a treatment of tricuspid regurgitation that is configured to easily adjust the device position to precisely block the orifice of the tricuspid valve during the treatment.

The objectives of the present invention are not limited to the above-mentioned objectives, and other objectives that are not mentioned will be clearly understood by those skilled in the art from the following description.

In order to achieve the objectives, there is provided an assembly-type device for a treatment of tricuspid regurgitation according to the present invention, the device including: a fixing member for pulmonary artery, the fixing member being installed in the pulmonary artery; a connecting tube provided with a connecting tube lumen formed therein to be movable along a connecting wire; an assembly part provided with a first assembly coupled to a lower end of the fixing member for the pulmonary artery and a second assembly coupled to an upper end of the connecting tube, thus allowing the fixing member for the pulmonary artery and the connecting tube to be assembled together; a fixing member for inferior vena cava, the fixing member being coupled to a lower end of the connecting tube and installed in the inferior vena cava; and a blocking part coupled to one side of the connecting tube and obliquely passing through a tricuspid valve to block an orifice of the tricuspid valve.

A screw thread may be formed on an inner circumferential surface of the first assembly, and a screw thread corresponding to the screw thread of the first assembly may be formed on an outer circumferential surface of the second assembly so that the first assembly and the second assembly may be engaged with each other.

According to another exemplary embodiment, the first assembly may be spherical in shape, and the second assembly may be an elastic tong, having elasticity, in a shape of the tong surrounding the first assembly, and wherein the second assembly may be unfolded along an outer surface of the first assembly when the second assembly is pushed toward the first assembly, and then, may be returned to an original state by the elasticity.

According to yet another exemplary embodiment, the first assembly may be provided with a fastening groove formed on a side surface thereof, and the second assembly may be provided with a fastening protrusion formed on a side surface thereof, and wherein the fastening protrusion may be inserted into the fastening groove when the second assembly is pushed toward the first assembly so that the first assembly and the second assembly may be assembled together.

In addition, according to a preferred exemplary embodiment of the present invention, the assembly-type device for a treatment of tricuspid regurgitation may further include: a connecting wire assembly part including: a first connecting wire assembly coupled to one side of the first assembly and provided with a screw thread formed on an inner circumferential surface thereof; and a second connecting wire assembly coupled to an upper end of the connecting wire and provided with a screw thread corresponding to the screw thread formed in the first connecting wire assembly on an outer circumference thereof, wherein the connecting wire assembly part may be assembled in a screw-type engagement, and may be disassembled by rotating the connecting wire.

According to the preferred exemplary embodiment of the present invention, the fixing member for the pulmonary artery and the fixing member for the inferior vena cava may have a radial structure.

According to another preferred exemplary embodiment of the present invention, the fixing member for the pulmonary artery and the fixing member of the inferior vena cava may be configured as a ribbon shape.

In addition, according to the present invention, the assembly-type device for a treatment of tricuspid regurgitation may further include: a sheath tube having a tube shape and provided with a lumen formed therein into which the assembly-type device for the treatment of the tricuspid regurgitation may be inserted, wherein, when inserting into a patient's body, the assembly-type device for the treatment of the tricuspid regurgitation may be inserted into the sheath tube and moves in a folded state, and when removing the sheath tube upon reaching a target position, the assembly-type device for the treatment of the tricuspid regurgitation may be unfolded.

According to the preferred exemplary embodiment of the present invention, the blocking part may include: a supporting wire having both ends thereof coupled to the connecting tube; and a blocking membrane having one side thereof fixed to the connecting tube and supported by the supporting wire.

According to the another preferred exemplary embodiment of the present invention, the blocking part may be a blocking balloon in a form of a balloon that may be expanded or contracted, and wherein the blocking part may further include a balloon tube having an upper end thereof connected to and communicated with the blocking balloon, and a balloon-adjusting hub connected to another end of the balloon tube, installed outside the patient's body, and expanding or contracting the blocking balloon.

According to yet another preferred exemplary embodiment of the present invention, the blocking part may include: a ring-shaped wire installed for the connecting tube to be passed through and provided with a central axis formed obliquely to the connecting tube, and a blocking membrane connecting the connecting tube and the ring-shaped wire to each other.

The assembly-type device for the treatment of tricuspid regurgitation according to the present invention may be passed through the inferior vena cava, the tricuspid valve, and the pulmonary artery in sequence, so as to enable the blocking part to be simply positioned in the orifice of the tricuspid valve.

In addition, by using the assembly-type device for the treatment of tricuspid regurgitation according to the present invention, the tricuspid regurgitation may be efficiently treated with a non-invasive method and a short treatment time.

In addition, the blocking part may obliquely pass through the centerline of the orifice of the tricuspid valve to stably block the orifice of the tricuspid valve.

In addition, fixing members are fixed to the pulmonary artery and the inferior vena cava so that the position of the blocking part is not affected by the movement of the diaphragm during breathing.

In addition, the assembly-type device for the treatment of tricuspid regurgitation according to the present invention has little interaction with the chordae tendineas or the papillary muscle, which are the substructure of the tricuspid valve, thereby having no possibility of problems caused by the interaction.

In addition, since the present invention provides a device being assembled inside the patient's body, the blocking part may be precisely positioned in the orifice of the tricuspid valve, and thus a customized treatment may be possible according to the patient.

DETAILED DESCRIPTION OF THE INVENTION

Benefits and features of the present invention and methods of accomplishing the same may be understood more readily by reference to the following detailed description of exemplary embodiments and the accompanying drawings. However, the present disclosure may be embodied in many different forms, and should not be construed as being limited to the exemplary embodiments set forth herein. Rather, these exemplary embodiments are provided so that this disclosure will be thorough and complete and will fully convey the concept of the invention to those skilled in the art, and the present disclosure will only be defined by the appended claims.

Hereinafter, the preferred exemplary embodiments of the present invention will be described in detail with reference to the accompanying drawings.

An assembly-type device for a treatment of tricuspid regurgitation according to the present invention is a device in which components are assembled in a patient's body, and the position of a blocking part is easily adjusted according to the patient, thereby treating tricuspid regurgitation by blocking an orifice formed by incomplete closing of the tricuspid valve.

Figure 1:
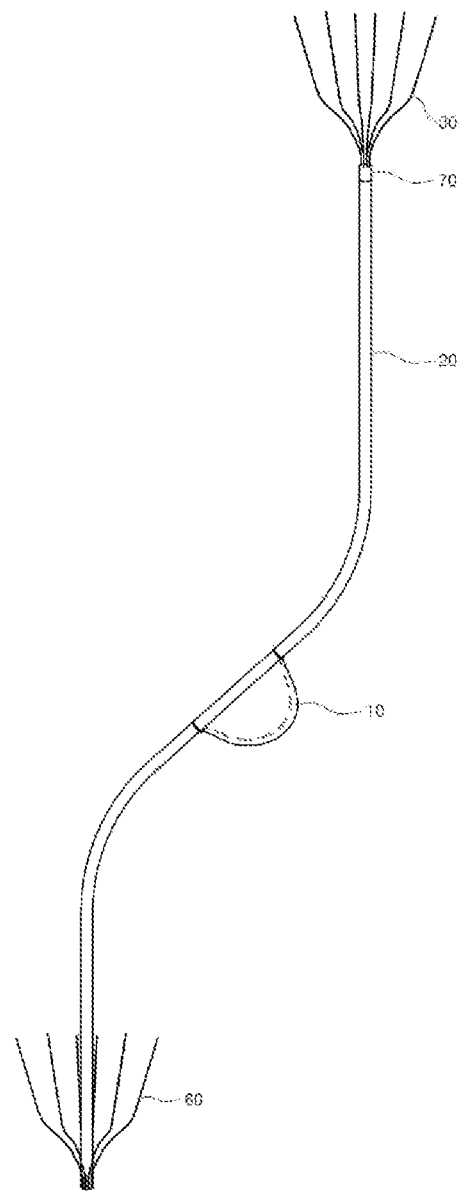
FIG. 1 is a perspective view of an assembly-type device for a treatment of tricuspid regurgitation according to a preferred exemplary embodiment of the present invention.

FIG. 1 is a perspective view of the assembly-type device for the treatment of tricuspid regurgitation according to the preferred exemplary embodiment of the present invention.

Referring to FIG. 1, the assembly-type device for the treatment of tricuspid regurgitation according to the preferred exemplary embodiment of the present invention includes a blocking part 10, a connecting tube 20, a fixing member for the pulmonary artery 30, a fixing member for the inferior vena cava 60, and an assembly part 70.

First, referring to the fixing member for the pulmonary artery 30 according to the preferred exemplary embodiment of the present invention, the fixing member for the pulmonary artery 30 is installed in the pulmonary artery, is provided with a lower end thereof coupled to the assembly part 70, and has a radial structure.

The fixing member for the pulmonary artery 30 may be made of a metal wire (i.e., stainless steel, nylon coating on metal, etc.), and is composed of a shape memory alloy, an elastic body, or a self-expandable stent.

The self-expandable stent refers to a stent capable of self-expansion with a frame made of Nitinol alloy.

The lower end of the fixing member for the pulmonary artery 30 is coupled to the assembly part 70, and the upper end thereof unfolds radially upward and is inserted in a folded state when inserted into a sheath tube 40 for insertion into the patients' body. When reaching a target position of the pulmonary artery and protruding out of the sheath tube 40, the fixing member for the pulmonary artery 30 is unfolded and returned to its original state, and is installed in the pulmonary artery.

The sheath tube 40 has the same shape as a general purpose catheter and is provided with a lumen into which the assembly-type device for the treatment of tricuspid regurgitation is inserted.

The sheath tube 40 is formed long enough to be operated at a position of the patient's thigh by an operator. The material of the sheath tube 40 may be synthetic resin material such as rubber, soft plastic, etc., and is made of a material having high flexibility and excellent resilience to be movable according the heartbeat.

The assembly part 70 coupled to the lower end of the fixing member for the pulmonary artery 30 may have a polygonal column shape such as a triangular column shape, a square column shape, or the like, but preferably has a cylindrical shape.

Detailed description of the assembly part 70 will be described with reference to FIG. 2.

Figure 2:
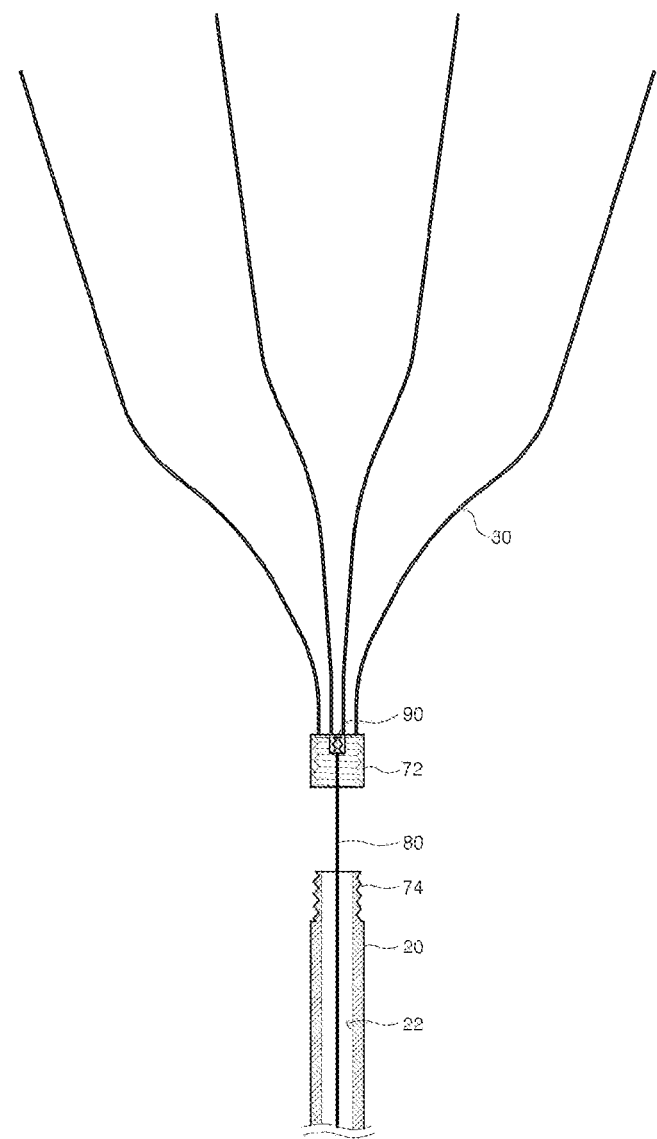
FIG. 2 is a perspective cross-sectional view of an assembly part according to the preferred exemplary embodiment of the present invention.

FIG. 2 is a perspective cross-sectional view of the assembly part according to the preferred exemplary embodiment of the present invention. Referring to FIG. 2, the assembly part 70 includes a first assembly 72 and a second assembly 74.

The first assembly 72 has a shape (Π) recessed upwardly from the bottom surface thereof, the top surface thereof is closed and the bottom surface thereof is open. A screw thread is famed on the inner circumferential surface of the first assembly 72.

In addition, the connecting wire assembly part 90 is coupled to the inner upper surface of the recessed space of the first assembly 72. One end of the connecting wire 80 is coupled to the bottom surface of the connecting wire assembly part 90, and a detailed description of the connecting wire assembly part 90 will be described in more detail with reference to FIG. 3.

The second assembly 74 is coupled to the upper end of the connecting tube 20, wherein, on the outer circumferential surface of the second assembly, a screw thread corresponding to the screw thread formed on the first assembly 72 is formed, and the inside thereof has a cavity so that the connecting wire assembly part 90 and the connecting wire 80 are inserted.

The diameter of the second assembly 74 is preferably smaller than the diameter of the first assembly 72. Thus, the second assembly 74 is inserted into the recessed space of the first assembly 72 and engaged with each other. First, the diameter of the first assembly 72 inserted into the patient's body is to be greater than the diameter of the second assembly 74, so that the treatment is more convenient.

The first assembly 72 and the second assembly 74 is made of a rigid metal (i.e., stainless steel, nylon coating on the metal) or plastics to facilitate to be engaged with each other.

In the case when the first assembly 72 and the second assembly 74 are engaged with each other more than half, the assembly part 70 has a binding power with such a degree that disassembly thereof by the movement of the heart is prevented.

Therefore, the second assembly 74 is further rotatable after being coupled with the first assembly 72. At this time, it is desirable that the direction of rotation of the second assembly 74 is in the direction that may be better coupled to the assembly part 70. As the operator moves the connecting tube 20 to the left and right, the second assembly 74 is rotated and the blocking part 10 coupled to the connecting tube 20 is moved to the left and right, so that the position of the blocking part 10 is adjusted.

Referring back to FIG. 1, the connecting tube 20 has a connecting tube lumen 22 formed therein to move along the connecting wire 80. The diameter of the connecting tube 20 is preferably formed the same as the second assembly 74, but is not limited thereto.

The connecting tube 20 may be synthetic resin material such as rubber, soft plastic, etc., and is made of a material having high flexibility and excellent resilience to be movable according to the heartbeat.

The second assembly 74 is coupled to the upper end of the connecting tube 20, and the fixing member for the inferior vena cava 60 is coupled to the lower end thereof.

The fixing member for the inferior vena cava 60 is to be installed in the inferior vena cava, wherein the lower end thereof is coupled along the outer circumferential surface of the connecting tube 20 at the lower end of the connecting tube 20, and the upper end thereof is formed in a radial structure which is unfolded upward of the connecting tube 20.

The fixing member for the inferior vena cava 60 may be made of a metal wire (i.e., stainless steel, nylon coating on metal, etc.), and is composed of a shape memory alloy, an elastic body, or a self-expandable stent.

The self-expandable stent refers to a stent capable of self-expansion with a frame made of Nitinol alloy.

The fixing member for the inferior vena cava 60 is inserted in a deformed shape when inserted into the sheath tube 40 for insertion into the patient's body, is returned to its original state when the sheath tube 40 is removed, and is installed to the inferior vena cava.

The blocking part 10 blocks the orifice by obliquely passing through the orifice of the tricuspid valve, and is coupled to one side of the connecting tube 20.

The blocking part 10 includes a supporting wire 14 having both ends thereof coupled to the connecting tube 20, and includes a blocking membrane 12 having one side thereof fixed to the connecting tube 20 and supported by the supporting wire 14.

When inserted into the sheath tube 40, the blocking part 10 is unfolded and inserted in a form surrounding the outer circumferential surface of the connecting tube 20. Various exemplary embodiments of the blocking part 10 will be described in detail with reference to FIGS. 7A to 7C described below.

Figure 3:
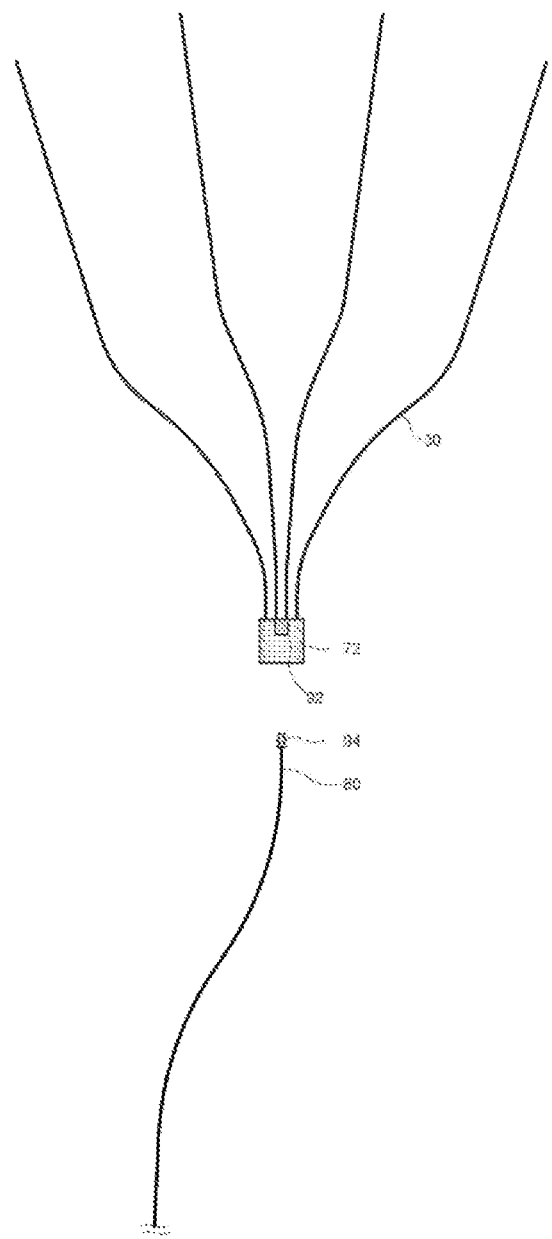
FIG. 3 is a cross-sectional view of a connecting wire assembly part according to the preferred exemplary embodiment of the present invention.

FIG. 3 is a cross-sectional view of the connecting wire assembly part according to the preferred exemplary embodiment of the present invention. Referring to FIG. 3, the connecting wire assembly part 90 includes a first connecting wire assembly 92 and a second connecting wire assembly 94. The connecting wire assembly part 90 is preferably formed in a cylindrical shape.

The first connecting wire assembly 92 is preferably coupled to the inner upper surface of the recessed part of the first assembly part 72 as described above, but is not limited thereto.

The first connecting wire assembly 92, having a shape (Π) recessed upward from the lower surface thereof, has the same shape as the first assembly 72. A screw thread is formed on the inner circumferential surface of the recessed part.

The second connecting wire assembly 94 is provided with a screw thread formed at a position on the outer circumferential surface thereof and corresponding to a screw thread of the first connecting wire assembly 92. The first connecting wire assembly 92 and the second connecting wire assembly 94 are engaged with each other.

The connecting wire 80 has an upper end thereof bonded to the lower surface of the second connecting wire assembly 94, and a lower end thereof formed long enough to be positioned outside of the patient's body through the thigh. The connecting wire 80 is composed of the same material as a guidewire 50, and is made of synthetic resin such as nylon, or metal wire (i.e., stainless steel, nylon coating on metal, etc.), and the like.

The connecting wire 80 is rotated at a position outside the patient's body to enable the connecting wire assembly part 90 to be coupled or disassembled.

Figure 4:
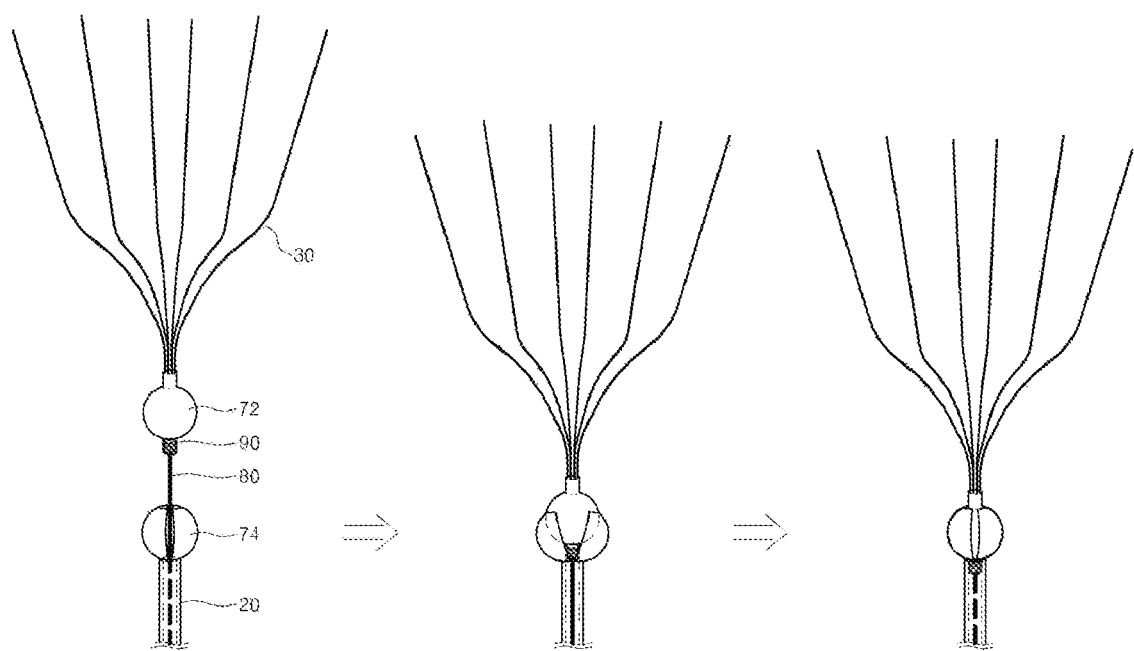
FIG. 4 is a view showing an assembly part according to another exemplary embodiment of the present invention, in which a second assembly part is coupled to a first assembly part.

FIG. 4 is a view showing a first assembly part and a second assembly part according to another exemplary embodiment of the present invention, wherein the second assembly part is coupled to the first assembly part.

Referring to the assembly part 70 according to the another preferred exemplary embodiment of the present invention, the first assembly 72 is preferably formed in a spherical shape, and is composed of a rigid material such as metal or rigid plastic.

The second assembly 74 has elasticity with a shape of a rounded tong to surround the first assembly 72. When the operator pushes toward the first assembly 72, the second assembly 74 unfolds along a rounded outer surface of the first assembly 72 from the lower end thereof. Then, when reaching the upper end of the first assembly 72, the second assembly 74 is returned to its original state by elasticity. The final coupling state is that the second assembly 74 is coupled to surround the entire first assembly 72.

The coupling of the first assembly 72 and the second assembly 74 according to the another preferred exemplary embodiment of the present invention is not affected by the movement of the heart, but is rotatable to the left and right by the force exerted by the operator outside the patient's body. As the operator moves the connecting tube 20 to the left and right, the second assembly 74 is rotated to the left and right and the blocking part 10 coupled to the connecting tube 20 moves along the connecting tube 20, thereby the position of the blocking part 10 is capable of being adjusted.

In this case, the first connecting wire assembly 92 is coupled to the lower surface of the first assembly 72. The shapes of the connecting wire assembly part 90 and the connecting wire 80 are the same as described in detail with reference to FIG. 3.

Figure 5:
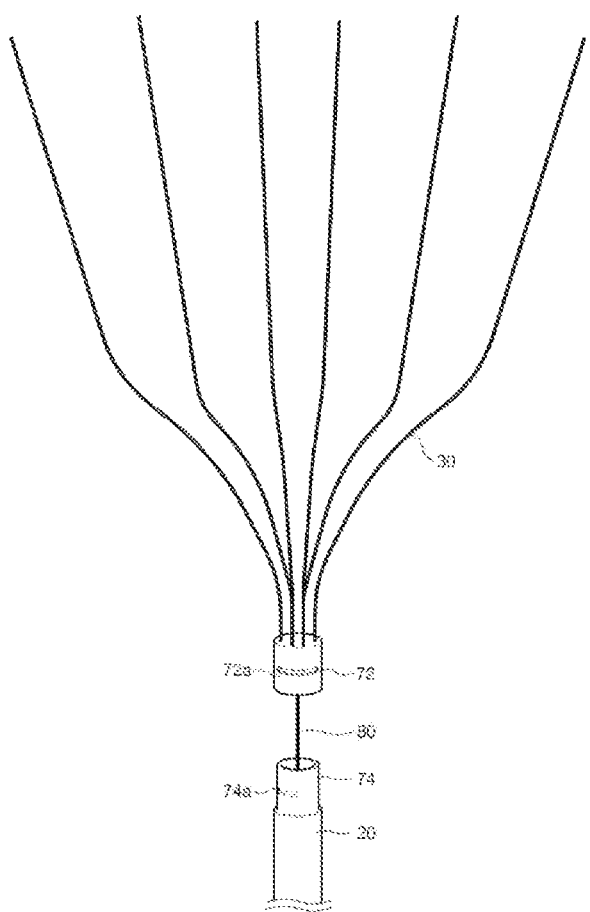
FIG. 5 is a perspective view of the assembly part according to yet another preferred exemplary embodiment of the present invention.

FIG. 5 is a perspective view of the assembly part according to yet another preferred exemplary embodiment of the present invention.

Referring to FIG. 5, the first assembly 72, according to the yet another preferred exemplary embodiment of the present invention, has a cylindrical shape provided with a fastening groove 72a on the side surface thereof, wherein the fastening groove 72a is provided longer in width than in height. Preferably, the first assembly 72 is recessed upward from the lower surface thereof, and the second assembly 74 is inserted into and coupled to the recessed part of the first assembly 72.

The second assembly 74, having a cylindrical shape, is preferably provided to have a diameter smaller than the diameter of the first assembly 72, and includes a fastening protrusion 74a provided at a position on one side of an outer circumferential surface thereof. The fastening protrusion 74a is elastic and has a lower part thereof provided thicker than the upper part thereof.

When the second assembly 74 is pushed upward to insert the second assembly 74 into the first assembly 72, the fastening protrusion 74*a* is pressed. Then, when the fastening protrusion 74*a* reaches the fastening groove 72*a*, the fastening protrusion 74*a* is returned to the unpressed state again. Thus, the assembly part 70 is assembled by engaging the fastening protrusion 74*a* with the fastening groove 72*a*.

The fastening protrusion 74*a* is not affected by the movement of the heart, and the coupling of the assembly part 70 is not disassembled. The fastening protrusion 74*a* is movable in the width direction within the fastening groove 72*a* by a force exerted by the operator outside the patient's body. As the operator moves the connecting tube 20 to the left and right, the second assembly 74 may be rotated to the left and right to adjust the position of the blocking part 10.

In addition, the second assembly 74 has a cavity therein, so that the connecting wire assembly part 90 or the connecting wire 80 is inserted. The first connecting wire assembly 92 is coupled to the upper surface of the recessed part of the first assembly 72, and the shape thereof is the same as described above in FIG. 3.

Figure 6:
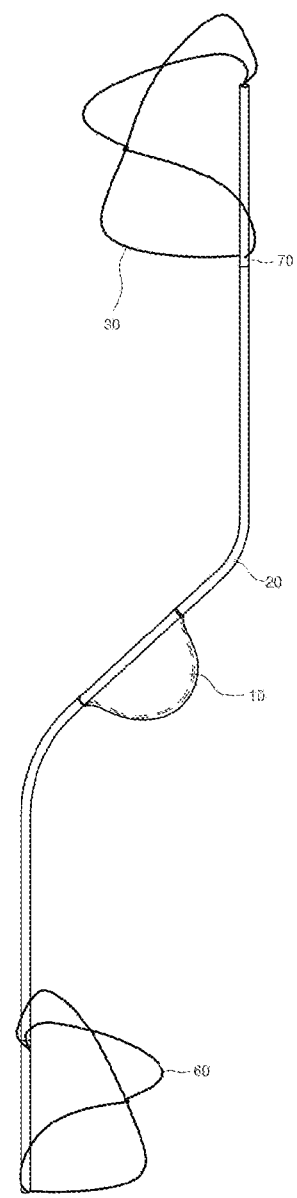
FIG. 6 is a perspective view showing the assembly-type device for the treatment of tricuspid regurgitation installed with another fixing member for the pulmonary artery and another fixing member for the inferior vena cava according to the present invention.

FIG. 6 is a perspective view showing the assembly-type device for the treatment of tricuspid regurgitation installed with another fixing member for the pulmonary artery and another fixing member for the inferior vena cava according to the present invention.

Referring to FIG. 6, each of the another fixing member for the pulmonary artery 30 and fixing member for the inferior vena cava 60 is respectively provided in a ribbon shape having a convex center, is made of a metal wire (i.e., stainless steel, nylon coating on metal, etc.), and is composed of a shape memory alloy, an elastic body, or a self-expandable stent.

The self-expandable stent refers to a stent capable of self-expansion with a frame made of Nitinol alloy.

When inserted into the sheath tube 40, the fixing member for the pulmonary artery 30 and the fixing member for the inferior vena cava 60 are deformed, and when the sheath tube 40 is removed, each of the central parts thereof is returned to a ribbon shape with a convex center, and are respectively installed in the pulmonary artery and inferior vena cava.

Figures 7A, 7B, 7C:
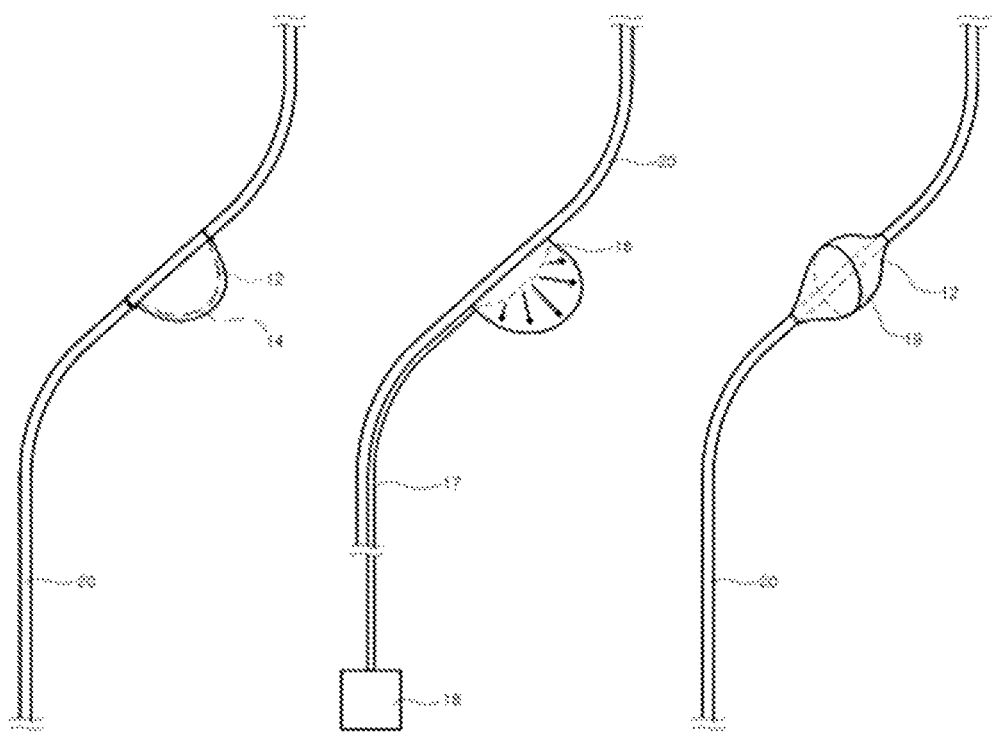
FIGS. 7A to 7C are perspective views showing an exemplary embodiment of various blocking parts according to the present invention.

FIGS. 7A to 7C are perspective views showing the exemplary embodiment of various blocking parts according to the present invention.

The blocking part 10 of FIG. 7A is composed of a blocking membrane 12 and a supporting wire 14 as described above with reference to FIG. 1, thereby blocking the orifice formed by incomplete closing of the tricuspid valve. Both ends of the supporting wire 14 are coupled to the connecting tube 20, and one side of the blocking membrane 12 is fixed to the connecting tube 20 and supported by the supporting wire 14.

The material of the supporting wire 14 may be synthetic resin such as nylon or metal wire (i.e., stainless steel, nylon coating on metal), and the like. The blocking membrane 12 has softness but is not easily torn, uses a material suitable for human body, and preferably is made of medical polyurethane, polyolefin, silicone, e-PTFE, PTFE, and the like. The blocking membrane 12 is made of one, two or more layers thereof.

When inserted into the sheath tube 40, the blocking part 10 of FIG. 7A is inserted in a form being surrounded on the outer circumferential surface of the connecting tube 20. Also, when removed from the sheath tube 40, the blocking part 10 is returned to its unfolded form and blocks the orifice of the tricuspid valve.

The blocking part 10 of FIG. 7B includes a blocking balloon 16, a balloon tube 17, and a balloon-adjusting hub 18. The blocking balloon 16 is installed at one side of the connecting tube 20 to block the orifice formed due to the incomplete closing of the tricuspid valve. One end of the balloon tube 17 is coupled to and communicates with the blocking balloon 16 while maintaining airtightness, and the other end of the balloon tube 17 is coupled to the balloon-adjusting hub 18 positioned outside the patient's body.

When the operator adjusts the balloon-adjusting hub 18 outside the patient's body and supplies air to the blocking balloon 16 through the balloon tube 17, the blocking balloon 16 is inflated. Also, when the air is removed, the blocking balloon 16 is reduced in size. The balloon-adjusting hub 18 injects air, oxygen, and form, and the supply amount is adjusted by the operator outside the patient's body, and thus the size of the blocking balloon 16 is changed in size. The size of the blocking balloon 16 may be adjusted according to the size of the orifice formed due to the incomplete closing of the tricuspid valve when the heart contracts.

The blocking part 10 of FIG. 7C includes a blocking membrane and a ring-shaped wire 19. The ring-shaped wire 19 is installed for the connecting tube 20 to pass through, the central axis thereof is formed obliquely with respect to the connecting tube 20, and the blocking membrane 12 connects the connecting tube 20 and the ring-shaped wire 19 to each other. Since the ring-shaped wire 19 has a central axis formed obliquely to the connecting tube 20, the ring-shaped wire 19 is positioned in parallel with the tricuspid valve inclined at a certain angle, thereby effectively blocking the orifice of the tricuspid valve. The ring-shaped wire 19 may be made of synthetic resin such as nylon or metal (i.e., stainless steel, nylon coating on metal), and the like. In addition, the material of the blocking membrane 12 is the same as the material of the blocking membrane of FIG. 7A.

FIGS. 8 to 12 show in order a method of treating by using the assembly-type device for the treatment of tricuspid regurgitation according to the preferred exemplary embodiment of the present invention.

Figure 8:
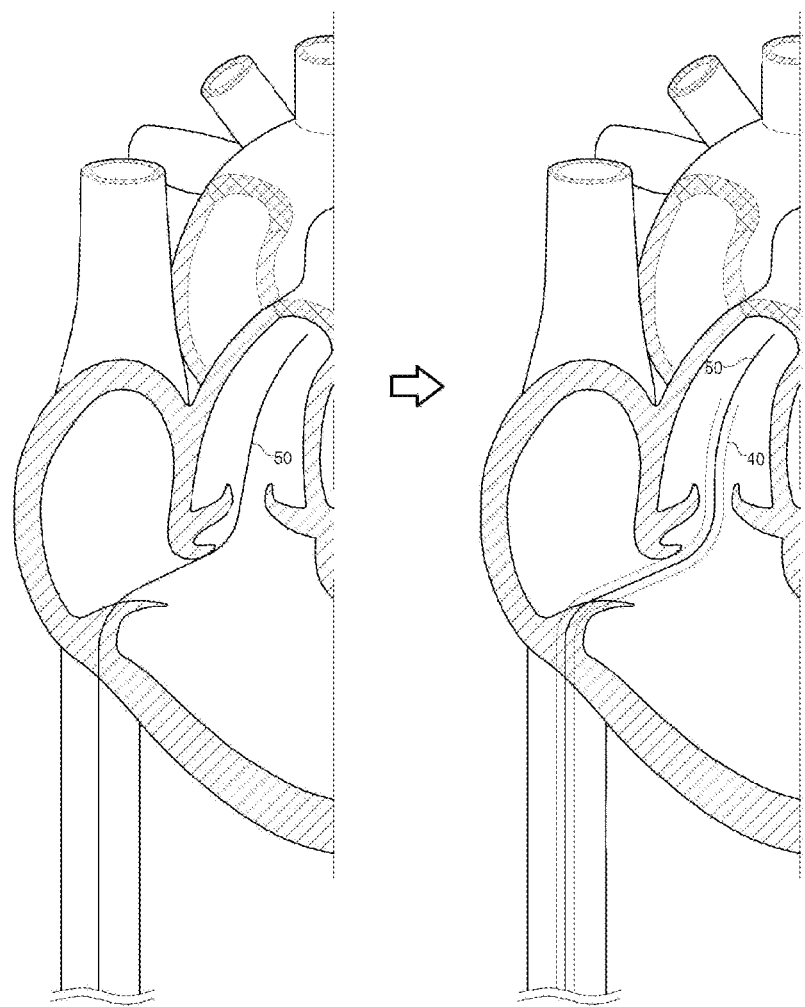
FIGS. 8 to 12 show in order a method of treating by using the assembly-type device for the treatment of tricuspid regurgitation according to the preferred exemplary embodiment of the present invention.

Referring to FIG. 8, the guidewire 50 is first inserted into the inferior vena cava, the tricuspid valve, and the pulmonary artery in sequence to provide a path for the assembly-type device for the treatment of tricuspid regurgitation, so as to easily move into the patient's body. The material of the guidewire 50 may be synthetic resin such as nylon or metal wire (i.e., stainless steel, nylon coating on metal, etc.), and the like. Also, it is desirable that the guidewire has a diameter of about 0.014".

Thereafter, the sheath tube 40 is inserted into the patient's body along the guidewire 50.

Figure 9:
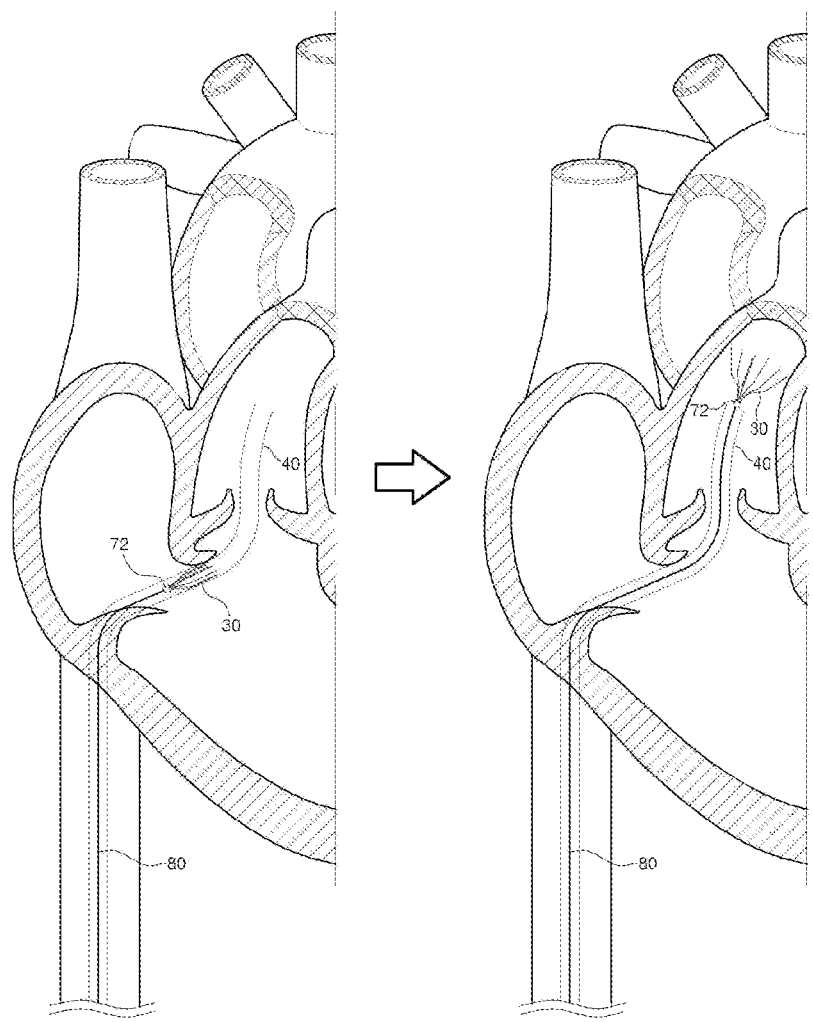

As shown in FIG. 9, after the guidewire 50 is removed, the fixing member for the pulmonary artery 30, the first assembly 72 coupled to the fixing member for the pulmonary artery 30, the connecting wire assembly part 90 coupled to the first assembly 72, and the connecting wire 80 coupled to the connecting wire assembly part 90 are inserted into the sheath tube 40.

In this case, the lower end of the connecting wire 80 is positioned outside the patient's body and may be adjusted by the operator. By pushing the connecting wire 80 upwards, the fixing member for the pulmonary artery 30 is unfolded and installed in the pulmonary artery.

Figure 10:
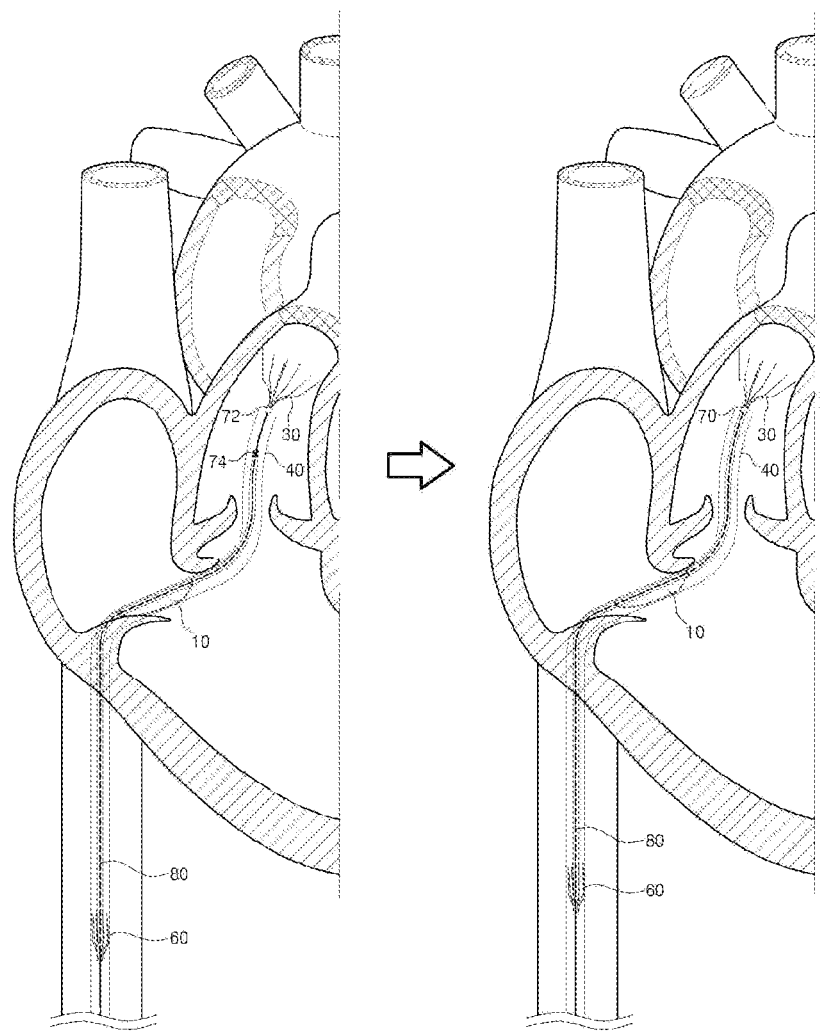

Next, as shown in FIG. 10, the connecting tube 20, the blocking part 10 coupled to one side of the connecting tube 20, fixing member for the inferior vena cava 60 coupled to the lower end of the connecting tube 20, and the second assembly 74 coupled to the upper end of the connecting tube 20 are inserted into the sheath tube 40.

At this time, the connecting wire 80 is inserted into the connecting tube 20 and moves into the patient's body along the connecting wire 80.

The blocking part 10 and the fixing member for the inferior vena cava 60 are inserted into the sheath tube 40 in a deformed state by being inserted into a general purpose catheter (not shown), and the general purpose catheter (not shown) is provided long to be operable at the thigh.

At this time, the sheath tube 40 is removed, and the blocking part 10 and the fixing member for the inferior vena cava 60, which are inserted into the general purpose catheter (not shown), may be inserted along the connecting wire 80.

By rotating or pushing the general purpose catheter (not shown) to assemble the second assembly 74 with the first assembly 72, the assembly-type device for the treatment of tricuspid regurgitation according to the present invention is made as one device. The general purpose catheter (not shown) is removed outside the patient's body in this stage.

Figure 11:
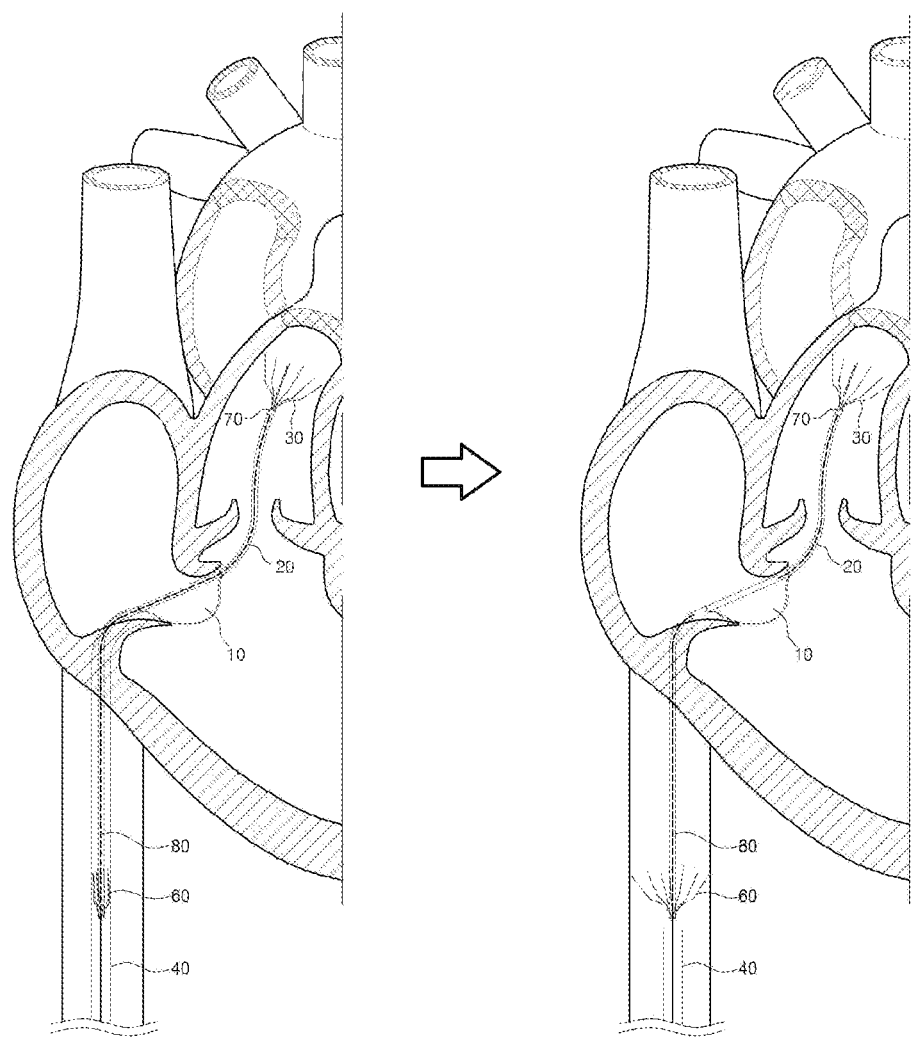

Thereafter, as shown in FIG. 11, the sheath tube 40 is pulled downward so that the blocking part 10 protrudes to the outside from the sheath tube 40. Then, the sheath tube 40 is adjusted to the left and right to rotate at the thigh so that the connecting tube 20 inserted into the sheath tube 40 is rotated. As the connecting tube 20 is rotated, the second assembly 74 coupled to the upper end of the connecting tube 20 is rotated, which does not affect the coupling force of the assembly part 70. In addition, as the connecting tube 20 is rotated, the blocking part 10 coupled to the connecting tube 20 is rotated so that the position of the blocking part 10 is adjusted.

The position of the blocking part 10 is adjusted to be positioned in the orifice of tricuspid valve, which varies depending on different patients, and then, by pulling the sheath tube 40 downward, the fixing member for the inferior vena cava 60 is unfolded and fixed to the inferior vena cava.

Figure 12:
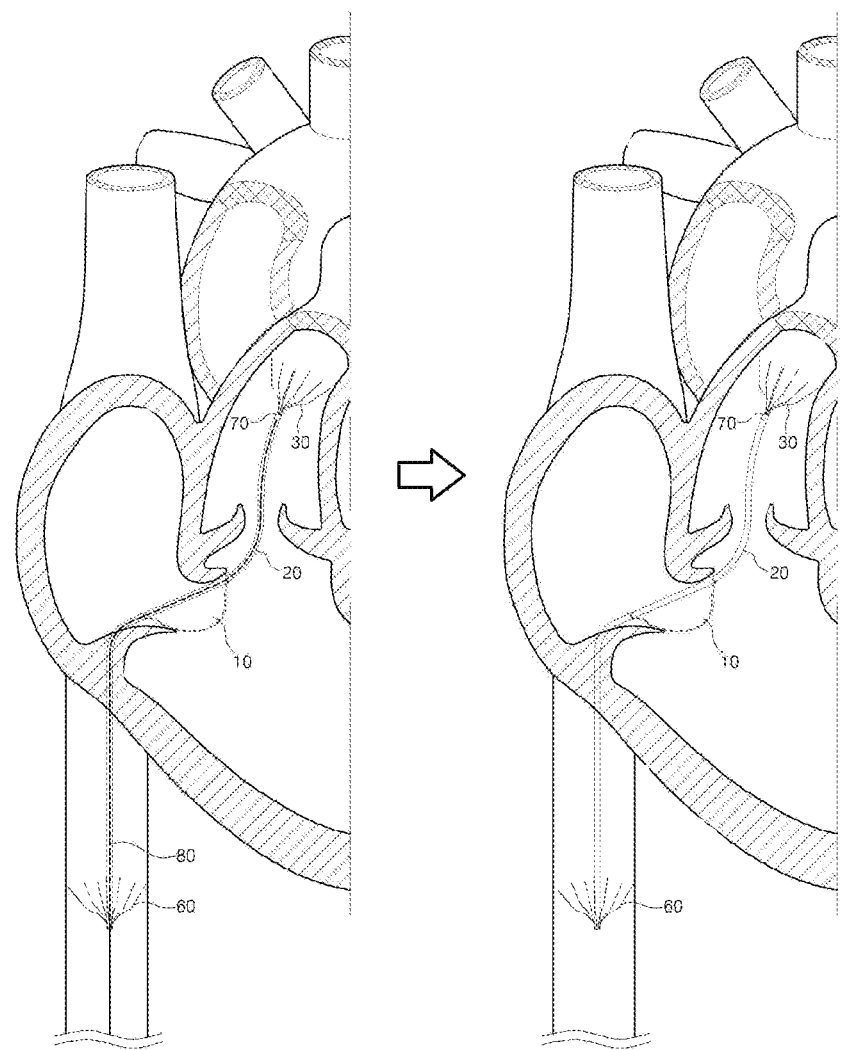

Finally, the sheath tube 40 is completely removed from the patient's body as shown in FIG. 12, and the screw connection of the connecting wire assembly part 90 is disassembled. Thereafter, the connecting wire 80 is removed out of the patient's body, and thus the assembly-type device for the treatment of tricuspid regurgitation according to the present invention is installed in the patient's body.

As described above, the assembly-type device for the treatment of tricuspid regurgitation according to the present invention is assembled in the patient's body, and the position of the blocking part is capable of being adjusted to be positioned precisely in the orifice of the tricuspid valve, whereby it is possible to perform customized treatment according to the patient.

Although the exemplary embodiments of the present invention have been described above with reference to the accompanying drawings, it will be understood that those skilled in the art to which the present invention pertains may implement the present invention in other specific forms without departing from the technical spirit or essential features thereof. Therefore, the exemplary embodiments described above are to be understood in all respects as illustrative and not restrictive.

What is claimed is:

1. A catheter device comprising:
    a distal fixing member configured for anchoring within the pulmonary artery;
    a connecting tube provided with a connecting tube lumen formed therein to be movable along a connecting wire;
    an assembly part provided with a first assembly coupled to a lower end of the distal fixing member and a second assembly coupled to an upper end of the connecting tube, whereby the distal fixing member and the connecting tube are coupled together;
    a proximal fixing member configured for anchoring within the inferior vena cava, the proximal fixing member being coupled to a lower end of the connecting tube; and
    a blocking part coupled to one side of the connecting tube;
    wherein the connecting tube has a distal bend with a first predetermined curvature at a location distal to the blocking part, wherein the first predetermined curvature is oriented in a first direction;
    wherein the connecting tube further has a proximal bend with a second predetermined curvature at a location proximal to the blocking part, wherein the second predetermined curvature is oriented in a second direction.

2. The device of claim 1, wherein a first screw thread is formed on an inner circumferential surface of the first assembly, and a second screw thread is formed on an outer circumferential surface of the second assembly, wherein the second screw thread corresponds with the first screw thread so that the first assembly and the second assembly are engaged with each other.

3. The device of claim 1, wherein the first assembly is spherical in shape, and the second assembly is an elastic tongs having elasticity, and in a shape of the tongs surrounding the first assembly, and wherein the second assembly is unfolded along an outer surface of the first assembly when the second assembly is pushed toward the first assembly, and then, is returned to an original state by the elasticity.

4. The device of claim 1, wherein the first assembly is provided with a fastening groove formed on a side surface thereof, and the second assembly is provided with a fastening protrusion formed on a side surface thereof, and wherein the fastening protrusion is inserted into the fastening groove when the second assembly is pushed toward the first assembly so that the first assembly and the second assembly is assembled together.

5. The device of claim 1, further comprising:
    a connecting wire assembly part comprising a first connecting wire assembly coupled to one side of the first assembly and provided with a screw thread formed on an inner circumferential surface thereof; and
    a second connecting wire assembly coupled to an upper end of the connecting wire and provided with a screw thread corresponding to the screw thread formed in the first connecting wire assembly on an outer circumference thereof, wherein the connecting wire assembly part is assembled in a screw-type engagement, and is disassembled by rotating the connecting wire.

6. The device of claim 1, wherein the distal fixing member and the proximal fixing member have a radial structure.

7. The device of claim 1, wherein the distal fixing member and the proximal fixing member are configured as a ribbon shape.

8. The device of claim 1, wherein the blocking part comprises:
    a supporting wire having both ends thereof coupled to the connecting tube; and
    a blocking membrane having one side thereof fixed to the connecting tube and supported by the supporting wire.

9. The device of claim 1, wherein the blocking part is a blocking balloon in a form of a balloon that may be expanded or contracted, and wherein the blocking part further comprises:
    a balloon tube having an upper end thereof connected to and communicated with the blocking balloon; and a balloon-adjusting hub connected to another end of the balloon tube and operable for expanding or contracting the blocking balloon.

10. The device of claim 1, wherein the blocking part comprises:
   a ring-shaped wire installed for the connecting tube to be passed through and provided with a central axis formed obliquely to the connecting tube, and
   a blocking membrane connecting the connecting tube and the ring-shaped wire to each other.

11. The device of claim 1, further comprising a sheath tube having a sheath lumen;
   wherein the catheter device is inserted through the sheath lumen;
   wherein the distal fixing member is in a folded configuration inside the sheath lumen;
   wherein the distal fixing member unfolds when exiting out of the sheath lumen.

12. The device of claim 1, wherein the second direction is different from the first direction.

13. The device of claim 12, wherein the second direction is opposite from the first direction.

14. The device of claim 13, the proximal bend is mirror symmetrical to the distal bend.

15. The device of claim 1, wherein the connecting tube consists of only a single bend proximal to the blocking part, wherein said single bend is the proximal bend.

* * * * *